(12) United States Patent
Stafford

(10) Patent No.: US 9,572,534 B2
(45) Date of Patent: Feb. 21, 2017

(54) DEVICES, SYSTEMS AND METHODS FOR ON-SKIN OR ON-BODY MOUNTING OF MEDICAL DEVICES

(75) Inventor: Gary Ashley Stafford, Hayward, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 806 days.

(21) Appl. No.: 13/171,401

(22) Filed: Jun. 28, 2011

(65) Prior Publication Data

US 2011/0319733 A1   Dec. 29, 2011

Related U.S. Application Data

(60) Provisional application No. 61/359,816, filed on Jun. 29, 2010.

(51) Int. Cl.
 *A61B 5/145* (2006.01)
 *A61B 5/00* (2006.01)
 *A61B 5/20* (2006.01)

(52) U.S. Cl.
CPC ......... *A61B 5/6833* (2013.01); *A61B 5/1451* (2013.01); *A61B 5/14507* (2013.01); *A61B 5/14532* (2013.01); *A61B 5/20* (2013.01)

(58) Field of Classification Search
CPC ......... A61B 5/68; A61B 5/145; A61B 5/6813; A61B 5/6839; A61B 5/14532; A61B 5/14552; A61B 5/1455
USPC ............... 600/309, 310, 322, 342, 344, 345, 347,600/365, 473, 476
See application file for complete search history.

(56) References Cited

U.S. PATENT DOCUMENTS

| | | |
|---|---|---|
| 3,123,790 A | 3/1964 | Tyler |
| 3,211,001 A | 10/1965 | Petit |
| 3,260,656 A | 7/1966 | Ross, Jr. |
| 3,581,062 A | 5/1971 | Aston |
| 3,653,841 A | 4/1972 | Klein |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |

(Continued)

FOREIGN PATENT DOCUMENTS

| | | |
|---|---|---|
| DE | 4401400 | 7/1995 |
| EP | 0098592 | 1/1984 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Tse Chen
*Assistant Examiner* — Chu Chuan (J J) Liu
(74) *Attorney, Agent, or Firm* — One LLP

(57) ABSTRACT

Devices, systems, methods and kits for releasably mounting a medical device on the body or skin of a user are provided.

38 Claims, 3 Drawing Sheets

(56) References Cited

U.S. PATENT DOCUMENTS

| | | |
|---|---|---|
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,908 A | 12/1986 | Miller |
| 4,633,878 A | 1/1987 | Bombardien |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,683 A | 11/1988 | Wozniak et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagata |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,002,054 A | 3/1991 | Ash et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |

(56) References Cited

U.S. PATENT DOCUMENTS

| | | |
|---|---|---|
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,462,645 A | 10/1995 | Albery et al. |
| 5,469,846 A | 11/1995 | Khan |
| 5,472,317 A | 12/1995 | Field et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,533,977 A | 7/1996 | Matcalf et al. |
| 5,543,326 A | 8/1996 | Heller et al. |
| 5,545,191 A | 8/1996 | Mann et al. |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halili et al. |
| 5,589,326 A | 12/1996 | Deng et al. |
| 5,593,852 A | 1/1997 | Heller et al. |
| 5,596,150 A | 1/1997 | Arndt et al. |
| 5,601,435 A | 2/1997 | Quy |
| 5,609,575 A | 3/1997 | Larson et al. |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,651,869 A | 7/1997 | Yoshioka et al. |
| 5,653,239 A | 8/1997 | Pompei et al. |
| 5,660,163 A | 8/1997 | Schulman et al. |
| 5,665,071 A | 9/1997 | Wyrick |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Renirie et al. |
| 5,743,262 A | 4/1998 | Lepper, Jr. et al. |
| 5,746,697 A | 5/1998 | Swedlow et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |
| 5,851,197 A | 12/1998 | Marano et al. |
| 5,858,001 A | 1/1999 | Tsals et al. |
| 5,865,804 A | 2/1999 | Bachynsky |
| 5,879,373 A * | 3/1999 | Roper ............... A61B 5/14552 600/322 |

(56) References Cited

U.S. PATENT DOCUMENTS

| | | |
|---|---|---|
| 5,885,211 A | 3/1999 | Eppstein et al. |
| 5,899,855 A | 5/1999 | Brown |
| 5,918,603 A | 7/1999 | Brown |
| 5,924,979 A | 7/1999 | Swedlow et al. |
| 5,925,021 A | 7/1999 | Castellano et al. |
| 5,931,868 A | 8/1999 | Gross et al. |
| 5,938,679 A | 8/1999 | Freeman et al. |
| 5,948,006 A | 9/1999 | Mann |
| 5,951,521 A | 9/1999 | Mastrototaro et al. |
| 5,951,582 A | 9/1999 | Thorne et al. |
| 5,954,643 A | 9/1999 | Van Antwerp |
| 5,954,685 A | 9/1999 | Tierney |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,049,727 A | 4/2000 | Crothall |
| 6,056,718 A | 5/2000 | Funderburk et al. |
| 6,059,946 A | 5/2000 | Yukawa et al. |
| 6,068,399 A | 5/2000 | Tseng |
| 6,071,391 A | 6/2000 | Gotoh et al. |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,144,837 A | 11/2000 | Quy |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,757 B1 | 10/2001 | Feldman et al. |
| 6,302,866 B1 | 10/2001 | Marggi |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,409,740 B1 | 6/2002 | Kuhr et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Roques |
| 6,440,068 B1 | 8/2002 | Brown et al. |
| 6,445,374 B2 | 9/2002 | Albert et al. |
| 6,461,496 B1 | 10/2002 | Feldman et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,522,927 B1 | 2/2003 | Bishay et al. |
| 6,540,891 B1 | 4/2003 | Stewart et al. |
| 6,546,268 B1 | 4/2003 | Ishikawa et al. |
| 6,551,494 B1 | 4/2003 | Heller et al. |
| 6,551,496 B1 | 4/2003 | Moles et al. |
| 6,554,795 B2 | 4/2003 | Lam et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,650,471 B2 | 11/2003 | Doi |
| 6,654,625 B1 | 11/2003 | Say et al. |
| 6,659,948 B2 | 12/2003 | Lebel et al. |
| 6,666,849 B1 | 12/2003 | Marshall et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,730,200 B1 | 5/2004 | Stewart et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Funderburk et al. |
| 6,758,810 B2 | 7/2004 | Lebel et al. |

(56) References Cited

U.S. PATENT DOCUMENTS

| | | |
|---|---|---|
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Ughigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,265 B2 | 5/2005 | Silver |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,462,264 B2 | 12/2008 | Heller et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,592 B2 | 10/2009 | Freeman et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,682,338 B2 | 3/2010 | Griffin |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,766,829 B2 | 8/2010 | Sloan et al. |
| 7,822,454 B1 | 10/2010 | Alden et al. |
| 7,866,026 B1 | 1/2011 | Wang et al. |
| 2002/0013538 A1 | 1/2002 | Teller |
| 2002/0019022 A1 | 2/2002 | Dunn et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0050250 A1 | 5/2002 | Peterson et al. |
| 2002/0055711 A1 | 5/2002 | Lavi et al. |
| 2002/0066764 A1 | 6/2002 | Perry et al. |
| 2002/0076966 A1 | 6/2002 | Carron et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0130042 A1 | 9/2002 | Moerman et al. |
| 2002/0133066 A1 | 9/2002 | Miller et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0165462 A1 | 11/2002 | Westbrook et al. |
| 2002/0169369 A1 | 11/2002 | Ward et al. |
| 2002/0198444 A1 | 12/2002 | Uchigaki et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |

(56) References Cited

U.S. PATENT DOCUMENTS

| | | |
|---|---|---|
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0072357 A1 | 4/2004 | Stiene et al. |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0116847 A1 | 6/2004 | Wall |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0140211 A1 | 7/2004 | Broy et al. |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0210122 A1 | 10/2004 | Sleburg |
| 2004/0223985 A1 | 11/2004 | Dunfield et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096520 A1 | 5/2005 | Maekawa et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0165404 A1 | 7/2005 | Miller |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0267327 A1 | 12/2005 | Iizuka et al. |
| 2005/0277164 A1 | 12/2005 | Drucker et al. |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047220 A1 | 3/2006 | Sakata et al. |
| 2006/0091006 A1 | 5/2006 | Wang et al. |
| 2006/0129173 A1 | 6/2006 | Wilkinson |
| 2006/0155210 A1 | 7/2006 | Beckman et al. |
| 2006/0155317 A1 | 7/2006 | List et al. |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0193375 A1 | 8/2006 | Lee |
| 2006/0195029 A1 | 8/2006 | Shults et al. |
| 2006/0200181 A1 | 9/2006 | Fukuzawa et al. |
| 2006/0200970 A1 | 9/2006 | Brister et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0253086 A1 | 11/2006 | Moberg et al. |
| 2006/0258929 A1 | 11/2006 | Goode, Jr. et al. |
| 2006/0264888 A1 | 11/2006 | Moberg et al. |
| 2006/0276724 A1 | 12/2006 | Freeman et al. |
| 2006/0282042 A1 | 12/2006 | Walters et al. |
| 2006/0287591 A1 | 12/2006 | Ocvirk et al. |
| 2007/0016381 A1 | 1/2007 | Kamath et al. |
| 2007/0027381 A1 | 2/2007 | Stafford |
| 2007/0038044 A1 | 2/2007 | Dobbles et al. |
| 2007/0056858 A1 | 3/2007 | Chen et al. |
| 2007/0068807 A1 | 3/2007 | Feldman et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0088377 A1 | 4/2007 | Levaughn et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0110124 A1 | 5/2007 | Shiraki et al. |
| 2007/0149875 A1 | 6/2007 | Ouyang et al. |

(56) References Cited

U.S. PATENT DOCUMENTS

| | | |
|---|---|---|
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0213611 A1 | 9/2007 | Simpson et al. |
| 2007/0219496 A1 | 9/2007 | Kamen et al. |
| 2007/0227911 A1 | 10/2007 | Wang et al. |
| 2007/0232879 A1 | 10/2007 | Brister et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004573 A1 | 1/2008 | Kaufmann et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0065646 A1 | 3/2008 | Zhang et al. |
| 2008/0066305 A1 | 3/2008 | Wang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0099332 A1 | 5/2008 | Scott et al. |
| 2008/0102441 A1 | 5/2008 | Chen et al. |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0148873 A1 | 6/2008 | Wang |
| 2008/0161664 A1 | 7/2008 | Mastrototaro et al. |
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262330 A1 | 10/2008 | Reynolds et al. |
| 2008/0262469 A1 | 10/2008 | Brister et al. |
| 2008/0267823 A1 | 10/2008 | Wang et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005659 A1 | 1/2009 | Kollias et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |

(56) References Cited

U.S. PATENT DOCUMENTS

| | | |
|---|---|---|
| 2009/0247856 A1 | 10/2009 | Boock et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0270765 A1 | 10/2009 | Ghesquire et al. |
| 2009/0287073 A1 | 11/2009 | Boock et al. |
| 2009/0287074 A1 | 11/2009 | Shults et al. |
| 2009/0294277 A1 | 12/2009 | Thomas et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2010/0004597 A1 | 1/2010 | Gyrn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0191082 A1 | 7/2010 | Brister et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204653 A1 | 8/2010 | Gyrn et al. |
| 2010/0212583 A1 | 8/2010 | Brister et al. |
| 2010/0213057 A1 | 8/2010 | Feldman et al. |
| 2010/0214104 A1 | 8/2010 | Goode et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode et al. |
| 2010/0240976 A1 | 9/2010 | Goode et al. |
| 2010/0261987 A1 | 10/2010 | Kamath et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0326842 A1 | 12/2010 | Mazza et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0082484 A1 | 4/2011 | Saravia et al. |
| 2011/0106126 A1 | 5/2011 | Love et al. |
| 2011/0118579 A1 | 5/2011 | Goode et al. |
| 2011/0118580 A1 | 5/2011 | Goode et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137257 A1 | 6/2011 | Gyrn et al. |
| 2011/0144465 A1 | 6/2011 | Shults et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190603 A1 | 8/2011 | Stafford |
| 2011/0190614 A1 | 8/2011 | Brister et al. |
| 2011/0191044 A1 | 8/2011 | Stafford |
| 2011/0201910 A1 | 8/2011 | Rasdal et al. |
| 2011/0201911 A1 | 8/2011 | Johnson et al. |
| 2011/0213225 A1 | 9/2011 | Bernstein et al. |
| 2011/0218414 A1 | 9/2011 | Kamath et al. |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |

(56) References Cited

U.S. PATENT DOCUMENTS

| | | |
|---|---|---|
| 2011/0288574 A1 | 11/2011 | Curry et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2012/0108983 A1 | 5/2012 | Banet et al. |
| 2012/0123385 A1 | 5/2012 | Edwards et al. |
| 2012/0296327 A1 | 11/2012 | Hutchins et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2004-520103 | 7/2004 |
| WO | WO-96/39977 | 5/1996 |
| WO | WO-96/25089 | 8/1996 |
| WO | WO-96/35370 | 11/1996 |
| WO | WO-97/21457 | 6/1997 |
| WO | WO-98/05053 | 8/1998 |
| WO | WO-98/56293 | 12/1998 |
| WO | WO-99/33504 | 7/1999 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/50534 | 6/2002 |
| WO | WO-02/058537 | 8/2002 |
| WO | WO-03/028784 | 4/2003 |
| WO | WO-03/073936 | 9/2003 |
| WO | WO-03/076893 | 9/2003 |
| WO | WO-03/082091 | 10/2003 |
| WO | WO-2004/054445 | 7/2004 |
| WO | WO-2004/060436 | 7/2004 |
| WO | WO-2004/061420 | 7/2004 |
| WO | WO-2005/084534 | 9/2005 |
| WO | WO-2005/089103 | 9/2005 |
| WO | WO-2006/042811 | 4/2006 |
| WO | WO-2006/108809 | 10/2006 |
| WO | WO-2007/041069 | 4/2007 |
| WO | WO-2007/140783 | 12/2007 |
| WO | WO-2007/143225 | 12/2007 |
| WO | WO-2008/065646 | 6/2008 |
| WO | WO-2008/133702 | 11/2008 |
| WO | WO-2009/062675 | 5/2009 |
| WO | WO-2010/112521 | 10/2010 |
| WO | WO-2011/002815 | 1/2011 |

OTHER PUBLICATIONS

Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1071.

Bennion, N., et al., "Alternate Site Glucose Testing: A Crossover Design", *Diabetes Technology & Therapeutics*, vol. 4 No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56 No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based Results on Wired Enzyme™ Technology-Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

(56) References Cited

OTHER PUBLICATIONS

Quinn, C. P., et al., "Kinetics of Glucose Delivery to Subcuraneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidt, F. J., et al., "Calibration of a Wearable Glucose Sensor", *The International Journal of Artificial Organs*, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Biosensor for Glucose", *Clinical Chemistry*, vol. 38, No. 9, 1992, pp. 1613-1617.
Alcock, S. J., et al., "Continuous Analyte Monitoring to Aid Clinical Practice", *IEEE Engineering in Medicine and Biology Magazine*, 1994, pp. 319-325.
Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.
Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.
Gregg, B. A., et al., "Cross-Linked Redox Gels Containing Glucose Oxidase for Amperometric Bionsensor Applications", *Analytical Chemistry*, vol. 62, No. 3, 1990, pp. 258-263.
Gunasingham, et al., "Electrochemically Modulated Optrode for Glucose", *Biosensors & Bioelectronics*, vol. 7, 1992, pp. 353-359.
Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.
Heller, A., "Electrical Connection Enzyme Redox Centers to Electrodes", *Journal of Physical Chemistry*, vol. 96, No. 9, 1990, pp. 3579-3587.
Ikeda, T., et al., "Artificial Pancreas—Investigation of the Stability of Glucose Sensors Using a Telemetry System" (English language translation of abstract), *Jpn. J. Artif. Organs*, vol. 19, No. 2, 1990, pp. 889-892.
Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.
Maidan, R., et al., "Elimination of Electrooxidizable Interferant-Produced Currents in Amperometric Biosensors", *Analytical Chemistry*, vol. 64, No. 23, 1992, pp. 2889-2896.
Mastrototaro, J. J., et al., "An Electroenzymatic Glucose Sensor Fabricated on a Flexible Substrate", *Sensors and Actuators B*, vol. 5, 1991, pp. 139-144.
Minimed Technologies, "Tape Tips and Other Infusion Site Information", 1995.
Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.
OHara, T. J., et al., "Glucose Electrodes Based on Cross-Linked $[Os(bpy)_2Cl]^{+/2+}$ Complexed Poly(1-Vinylimodazole) Films", *Analytical Chemistry*, vol. 65, No. 23, 1993, pp. 3512-3517.
Poitout, V., et al., "In Vitro and In Vivo Evaluation in Dogs of a Miniaturized Glucose Sensor", *ASAIO Transactions*, vol. 37, No. 3, 1991, pp. M298-M300.
Reach, G., et al., "Can Continuous Glucose Monitoring Be Used for the Treatment of Diabetes?", *Analytical Chemistry*, vol. 64, No. 6, 1992, pp. 381-386.
Rebrin, K., et al., "Automated Feedback Control of Subcutaneous Glucose Concentration in Diabetic Dogs", *Diabetologia*, vol. 32, 1989, pp. 573-576.
Ye, L., et al., "High Current Density 'Wired' Quinoprotein Glucose Dehydrogenase Electrode", *Analytical Chemistry*, vol. 65, No. 3, 1993, pp. 238-241.

* cited by examiner

DEVICES, SYSTEMS AND METHODS FOR ON-SKIN OR ON-BODY MOUNTING OF MEDICAL DEVICES

RELATED APPLICATION

The present application claims the benefit of U.S. provisional application No. 61/359,816 filed Jun. 29, 2010 entitled "Devices, Systems and Methods for On-Skin or On-Body Mounting of Medical Devices", the disclosure of which is incorporated herein by reference for all purposes.

BACKGROUND

There are many instances in which it is necessary to maintain a medical device "on-body", i.e., secured to a body part of a patient, e.g., the skin of an arm, abdomen, or elsewhere. One such instance is maintaining a component of an analyte monitoring system, e.g., a continuous analyte monitoring system, on the skin of a patient. Monitoring of the level of certain analytes may be vitally important to the health of certain individuals. In this regard, devices and systems have been developed for continuous or automatic monitoring of analytes in the blood stream or interstitial fluid. One common application of such analyte monitoring systems is in the monitoring and measurement of glucose levels in diabetic patients. Such measurements can be especially useful in monitoring and/or adjusting a treatment regimen, which may include the regular and/or emergent administration of insulin to the patient. Examples of such sensors and associated analyte monitoring systems can be found in U.S. Pat. Nos. 6,134,461; 6,175,752; 6,284,478; 6,560,471; 6,579,690; 6,746,582; 6,932,892; 7,299,082; 7,381,184; 7,618,369 and 7,697,967; and U.S. Patent Application Publication Nos. 2008/0161666, 2009/0054748, now U.S. Pat. No. 7,885,698, 2009/0247857, now U.S. Pat. No. 8,346,335, and 2010/0081909, now U.S. Pat. No. 8,219,173, the disclosures of each of which are incorporated by reference herein.

Many of these analyte monitoring systems include an in vivo sensor that is configured so that at least a portion of the sensor is positioned below the skin, e.g., in a blood vessel or in the subcutaneous tissue of a patient. The sensor communicates analyte information to a component positioned above the skin where, in certain embodiments, the component is intended to be maintained or worn on the skin of the patient. This on-skin or external component, in many systems, includes a control unit which has a housing which typically contains most or all of the electronic components of the analyte monitoring system. The housing is typically configured to couple or mate with one or more other portions of the control unit and with the sensor, or otherwise allows passage of the sensor therethrough, while providing electrical contact between the control unit electronics and the sensor.

Implantable or partially implantable sensors are almost always single-use devices with a limited useful sensing life, for example between about 3 and about 10 days, while the electronic components of a sensor system are typically reusable. As such, multiple sensors are used and replaced using the same on-skin/on-body control unit, thus requiring numerous physical and electrical couplings and decouplings between the control unit and sensors. Replacement of the control unit battery also requires some decoupling and recoupling of at least a portion of the control unit. Accordingly, it is important that the mechanisms and/or structures that enable the repeated coupling and decoupling of components be reliable and durable, yet easy enough for a patient to manipulate.

With the increasing popularity and use of on-skin or on-body medical devices, such as continuous analyte monitoring devices, there continues to be an interest in improving the structures by which and the manner in which the on-skin/on-body components of medical devices, are coupled/decoupled/recoupled to/from the skin and/or to each other.

SUMMARY

Generally, the present disclosure includes devices, systems, methods and kits for retaining a medical device on-body and/or removing a medical device from an on-body position and/or coupling/decoupling one or more portions of a medical device. Many of the inventive features facilitate removing disposable components from the reusable components of the medical device, such as when the disposable component, e.g., an implantable component, battery, etc., has reached its useful operative life or has expired.

Embodiments include a holder or mounting unit or structure that retains a medical device in a fixed position on a body part of a user or host, such as on the surface of the skin, and/or provides physical and/or electrical coupling to one or more additional components which may be operatively positioned above and/or below the surface of the skin. In certain embodiments, the medical devices are analyte monitoring systems which include an analyte sensor which is at least partially implantable below the skin surface and an analyte sensor control unit which is positionable above the skin surface.

In certain embodiments, the subject holders or mounting structures include a first portion and a second portion, wherein the second portion is moveable relative to the first portion for releasing at least a portion of the medical device from the structure when operatively mounted thereon. The holders or structures may further include a third portion extending between the first and second portions, wherein the third portion is configured to be alterable from a first state to a second state to provide the relative movement of the second portion to the first portion. In some of these embodiments, the third portion is returnable to the first state upon being altered to the second state, while in others, the third portion is not returnable to the first state upon being altered to the second state, for purposes, for example, of rendering the holder/structure inoperable to prevent its re-use.

In other embodiments, the subject holders or mounting units may be transformable from a first state to a second state, e.g., by a medical device release feature, or otherwise. A first state may include a useable state and a second state may include a release and/or an un-useable state. In certain embodiments, at least a portion of a holder is moved axially, rotationally, pivotally and/or arcuately relative to at least another portion of the holder after a medical device has been attached to the holder, and the movement of the at least one portion of the holder relative to another enables detachment of the medical device or a component thereof from the holder.

Additional embodiments provide assemblies including a medical device and a holder or mounting unit for releasably retaining the medical device on the body of a user, where the medical device and the mounting unit are cooperatively configured to releaseably and matingly engage with each other. In certain of these embodiments, the mounting unit includes a displaceable portion wherein displacement of the displaceable portion at least partially releases the medical device housing from the mounting unit. The displacement provided by the displaceable portion comprises one or more of linear, axial and angular movement. The displacement may be effected by a low-force pressure against the displaceable portion in a direction away from the medical device. The releasable coupling between the medical device and mounting unit may be provided by corresponding mating features on both components whereby effecting displacement of the displaceable portion decouples the corresponding mating features. A second pair of corresponding features for releasably coupling the medical device with the mounting unit may be provided wherein displacement of the displaceable portion of the mounting unit may or may not decouple the second corresponding features.

The present disclosure also includes methods, such as methods of using a medical device on the body of a host, which includes mounting the medical device on the body of the host by a mounting unit affixed to the skin surface of the host, operatively using the medical device for a predetermined period of time, and then displacing a first portion of the mounting unit relative to a second portion and thereby releasing the medical device from the mounting unit. Certain of the methods further include replacing at least one component of the medical device, returning the displaced first portion of the mounting unit to the first position, and operatively reusing the medical device for the predetermined period of time. Other methods include removing the medical device from the mounting unit, replacing at least one component of the medical device, mounting the medical device on the body of the host by means of a second mounting unit affixed to a second location on the skin surface of the host, and then operatively reusing the medical device for the predetermined period of time.

These and other objects, advantages, and features of the present disclosure will become apparent to those persons skilled in the art upon reading the details of the present disclosure as more fully described below.

BRIEF DESCRIPTION OF THE DRAWINGS

The present disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1A:
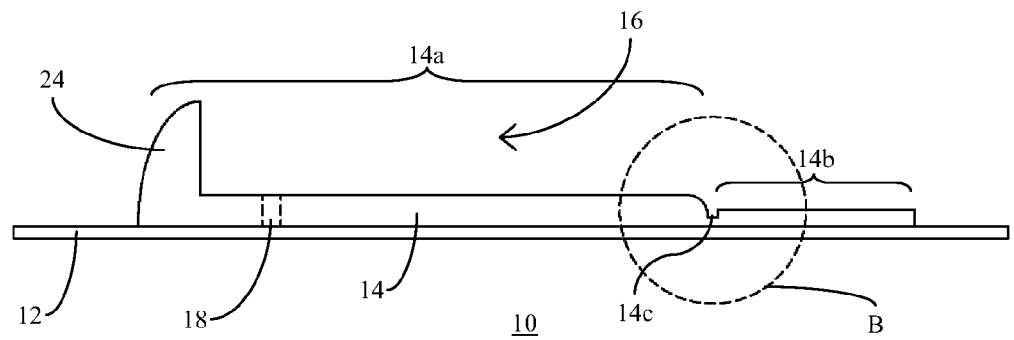
FIG. 1A illustrates a side view of a medical device holder according to an embodiment of the subject disclosure.

Before the present disclosure is described, it is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges as also encompassed within the present disclosure, subject to any specifically excluded limit in the stated range. Where the stated range includes one or both of the limits, ranges excluding either or both of those included limits are also included in the present disclosure.

Unless defined otherwise, all technical and scientific terms used herein have the same meaning as commonly understood by one of ordinary skill in the art to which the present disclosure belongs. Although any methods and materials similar or equivalent to those described herein can also be used in the practice or testing of the present disclosure, the preferred methods and materials are now described.

All publications mentioned herein are incorporated herein by reference to disclose and describe the methods and/or materials in connection with which the publications are cited. It is understood that the present disclosure supercedes any disclosure of an incorporated publication to the extent there is a contradiction. The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It must be noted that as used herein and in the appended claims, the singular forms "a", "an", and "the" include plural referents unless the context clearly dictates otherwise.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

As summarized above, embodiments of the present disclosure include devices and methods for maintaining a medical device in place on the body of a patient and/or removing a medical device from a body surface. Embodiments may be applicable to any medical device, including analyte monitoring devices and systems such as those using an analyte sensor (electrochemical, optical, etc.) wherein at least a portion of the sensor is positionable beneath the skin of the user or host for the in vivo determination of a concentration of an analyte in a body fluid, e.g., interstitial fluid, blood, urine, etc. Such an analyte sensor may be, for example, constructed to be at least partially subcutaneously (or elsewhere) positionable in a patient for the continuous and/or periodic monitoring of an analyte in a patient's interstitial fluid. The sensors also include in vivo analyte sensors positionable in a body vessel such as a vein, artery, or other portion of the body containing fluid. The sensors may have an ex vivo portion which is positionable outside the body, i.e., above the skin surface, and configured to be coupled to a component of the medical device system such as to a control unit housing mounted on the skin of the patient.

Sensors described herein may be configured for monitoring the level of the analyte over a time period which may range from minutes, hours, days, weeks, one month or longer. Of interest are analyte sensors, such as glucose sensors, that are capable of providing analyte data of a user for, and therefore have an in vivo operational life of, about one hour or more, e.g., about a few hours or more, e.g., about a few days of more, e.g., about three days or more, e.g., about five days or more, e.g., about seven days or more, e.g., about several weeks or months.

Analytes measurable by the subject sensors may include, but are not limited to glucose, lactate, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. Other of the subject sensors may be configured to detect and measure drugs, such as, for example, antibiotics (e.g., gentamicin, vancomycin, and the like), digitoxin, digoxin, drugs of abuse, theophylline, and warfarin. Two or more analytes and/or drugs may be monitored at the same or different times, with the same or different analyte sensor(s). If different sensors are employed, they may be coupled together, e.g., physically and/or electrically.

The subject analyte monitoring systems include an on-skin or external component having a housing which typically contains most or all of the electronic components of the analyte monitoring system, also referred to as a control unit. The on-body or on-skin control unit housing typically has a shape and profile which are comfortable for the patient and permit concealment. The housing often includes a base or mounting structure which is configured for engagement with the skin, such as by an adhesive layer, patch or strip, or by strapping it to the body. The control unit may include data processing and communication electronics, the latter of which may include a transmitter for relaying or providing data obtained using the sensor to another device such as a remotely located device. The control unit may also include a variety of optional components, such as, for example, a receiver, a power supply (e.g., a battery), an alarm system, a display, a user input mechanism, a data storage unit, a watchdog circuit, a clock, a calibration circuit, etc. A remote unit, if employed with the on-skin control unit, may include one or more of the same components and additional components such as an analyte measurement circuit for use with an in vitro sensor, a pager, a telephone interface, a computer interface, etc.

While embodiments of the subject disclosure are further primarily described with respect to analyte monitoring devices and methods such as glucose monitoring devices and methods, such description is in no way intended to limit the scope of the present disclosure. It is understood that the subject disclosure is applicable to any medical device in which at least a portion of the device is intended to be maintained in place on a patient for a predetermined period of time.

Embodiments of the subject holders/mounting units include a medical device area that connects a medical device to the holder, and a body attachment area that attaches the holder to a body part of a user, where the medical device and body attachment areas may be the same or different areas, including at least partially overlapping areas.

A medical device area may contain one or more features to attach a medical device to a holder, e.g., corresponding mateable features on a holder and a medical device, such as one or more clip(s), rail(s), hook(s), tab(s), groove(s), slot(s), guide(s), orifice(s), adhesive(s), and the like. For example, certain holder embodiments may include a pair of elongated, parallel side rails that slideably receive a medical device to anchor it to the holder. Embodiments may include a medical device that has a first mating member and a holder that has a second mating member, where the second mating member is adapted to mate with the first mating member so that the first and second mating members interlock or otherwise engage with each other. In an embodiment, the first mating member may include at least one tab positioned on or in the medical device. The second mating member may include a receiving area, e.g., that includes a depression or orifice or tunnel, or the like, and be positioned on or in a holder and which is adapted to mate with the least one tab so that the at least one tab and the receiving area cooperate together to form an interlocking structure that retains the medical device and holder together, e.g., by frictional engagement, snap fit engagement, or the like. First and second mating members may be selectively engageable and disengagable such that mated arrangement prevents separation of the medical device and the holder when engaged, but are otherwise easily disengageable when desired. Such ease of coupling and decoupling components is useful, for example, when a battery or sensor requires replacement.

A body attachment area may include one or more features, including, but not limited to, one or more of a strap, latch, adhesive, filaments or threads, or other fasteners, to maintain or anchor a holder and a held medical device on a body of a user such as an arm, leg, abdomen, etc. for a period of time such as the operating life of the sensor. Exemplary techniques and fasteners that may be employed include, but are not limited to, embodiments described in U.S. Pat. No. 6,175,752, and U.S. Patent Application Publication No. 2010/0049025, now U.S. Pat. No. 7,951,080, the disclosures of which are herein incorporated by reference. A holder may be secured to a body prior to or after attaching a medical device to the holder.

A holder may also include an area for interaction with an analyte sensor, e.g., a portion of a sensor that protrudes from the skin while a portion of the sensor is positioned beneath the skin (e.g., in the subcutaneous space, or the like). A holder may include one or more of a port, cavity, surface, protrusion, and/or other feature that receives or otherwise interacts with at least a portion of an analyte sensor. Embodiments of a holder may include a conductive material portion (e.g., metal, carbon, conductive polymer (carbon impregnated polymers, and the like), etc.) to electrically contact conductive material of a sensor and/or of a medical device to establish electrical connection. One or more moisture barriers may be provided to encompass this area about the electrical contacts of the sensor and the holder and/or medical device to provide resistance and/or impermeability to moisture, including preventing moisture ingress to the contacts and/or other electrical components of the holder and/or sensor and/or medical device. Moisture barriers include sealants that may include polymers such as elastomers and the like. Barriers may be malleable and may provide increased resistance to shock and/or vibration.

As described herein, a holder and/or medical device may include one or more structures, e.g., cooperating structures, to hold the medical device in a fixed position relative to an analyte sensor, and/or to the holder itself e.g., interlocking features, guide features, rail features, etc. Embodiments of the medical device holders include at least one medical device release feature that at least assists in, and in some embodiments completes, release of a medical device from the holder when the medical device is connected thereto. The one or more medical device release features may alter the holder when engaged to initiate release of a medical device. Altering, which may include breaking, the holder may cause the cooperating structures to be dissociated or released from each other so the medical device can be removed from the holder, e.g., slid away from the holder. Any of the holder-altering actions described may temporarily or reversibly or permanently alter a holder and/or medical device and/or sensor.

Embodiments include a displaceable area of a holder that is movable relative to the holder, e.g., twistable, or bent, or deformable, or otherwise flexed in one or more directions relative to an axis of the holder and/or relative to one or more other portions of the holder. Embodiments include a frangible or breakable area. A frangible area may include a weakened area such as an area of material that is less durable than a surrounding area. Some holders may include an area of reduced mass, material thickness, scoring, or the like. The area may include a gripping portion that enables an area of the holder to be displaced relative to at least one other area of the holder, permitting, including causing, a medical device held by the holder to be released and/or altering the holder to prevent further use.

In some embodiments, a holder may be a single use holder designed and intended and used to hold a single medical device, after which the holder is discarded. Certain embodiments include a reusable holder such that a given holder may be designed and intended and used to hold a first medical device, and at least a second, subsequent medical device, with the same or different analyte sensors. In order to render a holder operable, the detachable portion may be replaceable with itself (e.g., not completely destructed) after detachment or with another detachable portion in some instances.

In certain embodiments, a medical device release feature may include a medical device attachment feature, or vice versa, e.g., may be the same feature in some instances. In certain embodiments, altering of a holder may prevent continued use of the holder and/or medical device and/or sensor. For example, a feature may alter the physical and/or structural integrity of a holder (e.g., disfigure) so that it is unable to thereafter be used, e.g., unable to receive a sensor and/or couple a medical device and/or be secured to a body part and/or establish electrical communication. In certain embodiments in which a holder includes electrical contacts, altering may include rendering the electrical contacts unusable. This may include modifying one or more of the electrical contacts in shape and/or electrical conductivity, and the like. In certain embodiments, a holder may be reversibly altered, e.g., temporarily, or may be permanently altered. For example, a holder may be temporarily or permanently deformable. Embodiments that are reversibly altered may include a user intervention feature that requires a user to take action to render the holder useable once it has been rendered unusable, and in other embodiments, it may not require user intervention, e.g., may revert to an operable state automatically, e.g., after a certain action or period of time has occurred.

FIG. 1A illustrates an exemplary embodiment of an on-body medical device holder, base or mounting unit 10. Holder 10 includes a support body 14 adapted to be held on a skin surface of a user of a medical device 30 held by holder 10 (see FIG. 3A). Support body 14 may be flexible or rigid, and may include one or more flexible areas and/or one or more rigid areas. In the embodiment of FIG. 1A, holder 10 further includes an adhesive member 12 provided on the bottom surface of support body 14 for temporarily attaching holder 10 to a skin surface for a period of time, e.g., as described herein. Support body 14 includes a first or main portion 14a, a second or release portion 14b, which is shown in fragmented views in FIGS. 1B and 1C, and a third or transition portion 14c extending between the main and release portions 14a, 14b. Support body 14 may have a substantially planar construct having a bottom surface configured for placement on a skin surface and a top surface configured for receiving a medical device or a component thereof. Support body 14 may be provided in an initial state in which all portions thereof, i.e., portions 14a-c, are provided in the same plane and are coupled to each other in a serial fashion, e.g., end-to-end. In other embodiments, the various support body portions may physically overlap in parts, be stacked on top of each other, or one portion may partially or completely surround another portion. Referring again to FIG. 1A, the end of main portion 14a opposite break portion 14c and release portion 14b may provide an abutment structure or wall 24 to further support and retain a medical device 30 on holder 10 (see FIG. 3A). Abutment 24, as well as any other surfaces of holder 10, which are exposed after operative engagement with a medical device, may be curved, contoured, rounded, beveled or the like to provide a smooth, low profile.

Figure 1B:
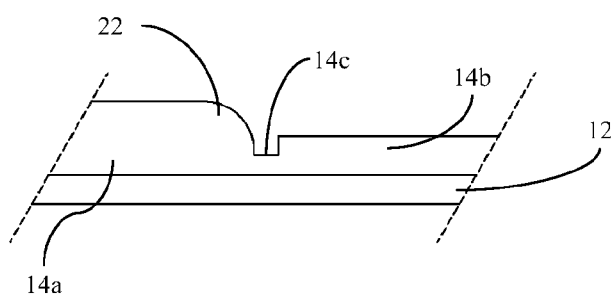
FIG. 1B illustrates an enlarged fragmented view of a portion of the holder of FIG. 1A denoted by area B.
Figure 1C:
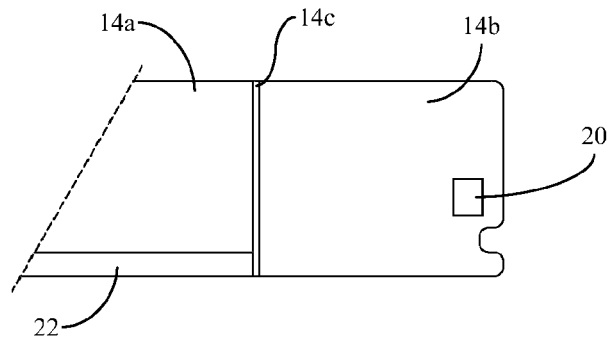
FIG. 1C illustrates an enlarged cutaway plan view of a portion of the holder of FIG. 1A.
Figure 3A:
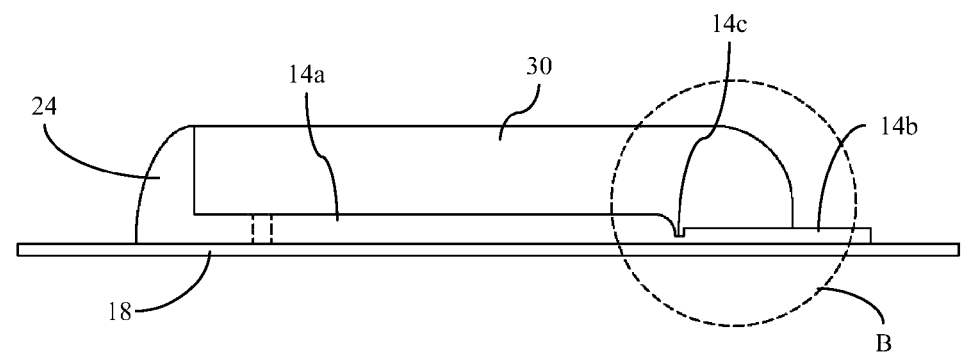
FIG. 3A illustrates the holder of FIGS. 1A-1C operatively holding a medical device.
Figure 3B:
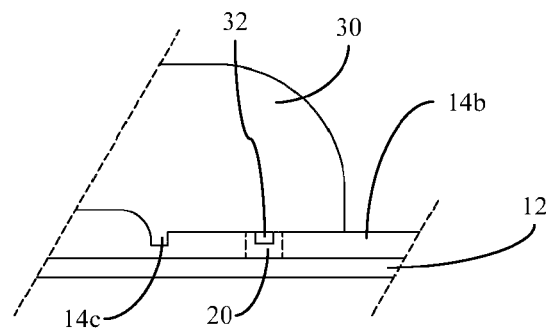
FIG. 3B illustrates an enlarged fragmented view of a portion of the holder and medical device denoted by area B of FIG. 3A.
Figure 4:
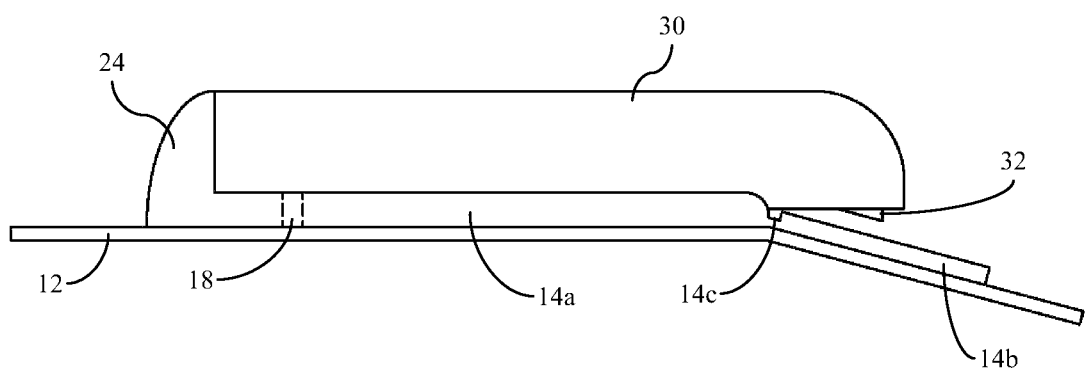
FIG. 4 illustrates the holder of FIGS. 1A-1C in a medical device release configuration.

As shown, for example in FIGS. 3A and 4, holder or base unit 10 is configured to retain a medical device 30 at medical device area 16 (e.g., in and/or on). For example, a medical device 30 may be attached to a holder 10 on a top surface of support body or unit 14 (see e.g., FIGS. 3A and 4). As discussed above, base unit 10 may further include at least one feature that is mateable with a corresponding locking feature on a medical device 30 which is intended to be mounted thereto. As shown in the embodiments of FIGS. 1A-1C, one such cooperating feature includes one or more rails 22 extending along the top surface of at least main portion 14a that are configured to engage one or more corresponding grooves (not shown) on the underside of the medical device. For example, a single rail may extend centrally along a main axis of holder 10 which corresponds to centrally extending groove (not shown) on the medical device, or a pair of spaced-apart, parallel rails may be provided on opposing sides of holder 10 corresponding to similarly situated grooves on the medical device. Rails 22 may extend over a first portion 14a and/or may extend over third portion 14c, but in many embodiments are absent from second portion 14b. Accordingly, in the illustrated embodiment, medical device 30 is mated with holder 10 by aligning a front end of its grooves (not shown) with the rear end of rails 22 and slideably advancing device 30, where such advancement may continue until it abuts end wall 24. Additionally or alternatively, as shown in FIGS. 1C and 3B, another holder, medical device mating or locking feature in the form of an aperture or receptacle 20 within release portion 14b, and a corresponding hook or tab 32 extending from a bottom surface medical device 30, may be provided. The coupling of these corresponding features may include a snap fit, friction fit or the like, to lock the movement of medical device 30 relative to holder 10. As discussed in greater detail below, in certain embodiments when holder 10 is altered and release portion 14b is displaced from medical device 30, tab 32 is released from aperture 20, as shown in FIG. 4, and medical device 30 may be removed from holder 10, e.g., by sliding it off of rails 22. In this manner, holder 10 securely yet removeably retains medical device 30.

In the case where medical device 30 includes an implantable or partially implantable glucose sensor, such as with an in vivo glucose monitoring system, holder 10 may also include a receiving area such as an aperture 18 (FIG. 1A) therethrough for guiding sensor insertion and/or providing secure electrical contact between the sensor and the sensor control unit to be mounted on holder 10. Receiving area or aperture 18 may be positioned in, on or at any of a number of areas of holder 10 including any one or more of portions 14a-c. In certain embodiments, receiving area or aperture 18 may include electrical contacts (not shown).

The various portions 14a-c of holder 10 may be made of the same or different material(s) and/or have the same or different thickness, stiffness, width, length and/or height dimensions. For example, in certain embodiments, enough material thickness may be in transition of break portion 14c to enable a medical device to be secured to support body 14, yet thin enough to enable holder 10 to be altered about portion 14c, e.g., to enable a low force displacement of portion 14b relative to portion 14a and/or portion 14c. In certain embodiments, portion 14c may have a material thickness about 50% or less of that of portions 14a and/or 14b. For example, if portions 14a/14b have a thickness dimension of about 1.0 mm, portion 14c has a thickness dimension of about 0.5 mm, requiring a force about 4 to about 12 Newtons to bend and/or break. In other embodiments, the thickness of portion 14c may be substantially less than 50% or more than 50% of the thickness of the other portions, requiring a lower or greater amount of force to break or bend. Transition portion 14c may otherwise include a hinge (e.g., a living hinge) that is connected to main portion 14a and release portion 14b to allow release portion 14b to pivot with respect to the main portion 14a. In other embodiments, transition portion 14c may include a weakened area, detent and/or fracture point. In certain of these embodiments, scores or perforations may be formed at intervals across portion 14c.

Accordingly, altering holder 10 may include any action resulting in the misalignment, e.g., linear, axial and/or angular misalignment, of portions 14a and 14b relative to each other. Such ability enables transitioning at least two portions of holder 10 from a medical device holding state in which the at least two portions are aligned with respect to each other to hold a medical device 30 (as shown in FIG. 3A) to a medical device release state in which the at least two portions of holder 10 are linearly misaligned or offset relative to each other to remove the medical device 30 from the holder 10 (as shown in FIG. 4). The medical device 30 may also be in the holding state for sensor insertion into the body of a user, and therefore the medical device holding state may be characterized as a medical device insertion state. Release portion 14b may be displaced in any direction relative to main portion 14a, e.g., may be moved in the x, y and/or z planes. In certain embodiments, release portion 14b may be limited to movement in only one direction, for example release portion 14b may be limited to movement in the x-plane direction, and in other embodiments, release portion 14b may be moveable in two or more directions. In some embodiment, moving release portion 14b may include pivoting it about a pivot point.

Figure 2:
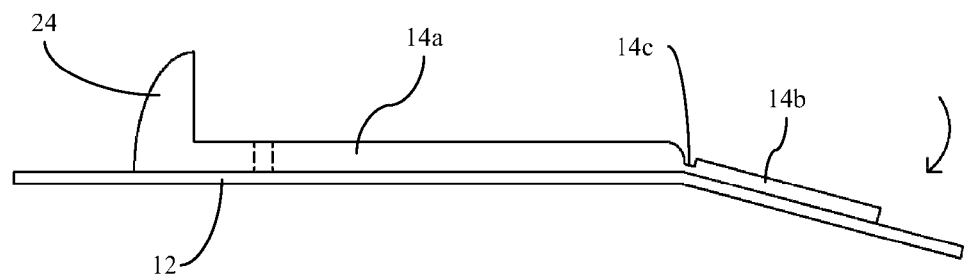
FIG. 2 illustrates the holder of FIGS. 1A-1C in a medical device release configuration.

For example, as shown in FIGS. 2 and 4, portion 14b is moveable, e.g., bendable, away from main portion 14a, by depressing release portion 14b, to enable medical device 30 to be removed from holder 10 after, for example, the in vivo operational life of the sensor has elapsed and/or the glucose sensor positioned in a user and being used with the system is otherwise no longer functional. Displacing release portion 14b may cause it to detach from portion 14a or at least enable it to be detached, or it may remain attached. In certain embodiments, second portion 14b may be displaced from about 1 to about 90 degrees, e.g., from about 1 to about 45 degrees. This angular displacement is typically accomplished with the application of a low force to release portion 14b, e.g., by light pressure from a finger.

In certain embodiments, displacement of release portion 14b relative to at least main portion 14a may cause medical device 30 to be at least partially decoupled or released from holder 10. This decoupling may further include at least initiating movement of medical device 30 in a release direction. For example, urging portion 14b in a transverse (or other) direction relative to portion 14a may cause medical device 30 to move, e.g., slide, away from a fully engaged, nested position within holder 10, such as that shown in FIG. 3A. In certain embodiments, holder 10 may be configured such that release and/or removal of medical device 30 from holder 10 is performed while holder 10 is operatively adhered or fixed to the skin surface, wherein in other embodiments release and/or removal of medical device 30 from holder 10 is performed while holder 10 is not operatively adhered or fixed to the skin surface. Further, medical device 30 may be configured to become inoperable or disabled upon decoupling or release from holder 10 in embodiments to prevent further use or limit application to only a single use.

It is evident from the above results and discussion that the above-described disclosure provides devices and methods for maintaining a medical device on-body. The above-described disclosure provides a number of advantages, some of which are described above and which include, but are not limited to, ease of use, even in instances in which the medical device is to be maintained on a body part that is not within the direct line of site of the patient, and comfort. Furthermore, the subject disclosure provides a patient with a high degree of confidence that the medical device is securely maintained in position on a body part. As such, the subject disclosure represents a significant contribution to the art.

In certain embodiments, a structure adapted for mounting a medical device on the body of a host may comprise a first portion, and a second portion moveable relative to the first portion, wherein movement of the second portion relative to the first portion causes release of at least a portion of a medical device from the first and second portions when operatively mounted thereon.

Certain aspects may include a third portion extending between the first and second portions, wherein the third portion is configured to be alterable from a first state to a second state to provide the movement of the second portion relative to the first portion.

In certain aspects, the third portion may be one of breakable, bendable, frangible or one or more combinations thereof.

In certain aspects, the third portion may comprise one or more of a reduced mass, a reduced thickness, a weakened area, a detent, a hinge, a fracture point or scoring.

In certain aspects, the third portion may be returnable to the first state upon being altered to the second state.

In certain aspects, the third portion may be not returnable to the first state upon being altered to the second state.

In certain aspects, the relative movement may comprise one or more of linear, axial and angular displacement.

Certain aspects may include at least one feature for releasably coupling with a corresponding at least one feature of the medical device.

Certain aspects may include a first surface configured for retaining the medical device.

Certain aspects may include a second surface for placement on a skin surface, wherein the first and second surfaces are on opposing sides of the structure.

In certain aspects, the second surface may comprise an adhesive.

In certain aspects, the first portion comprises an abutment for retaining the medical device.

Certain aspects may include an aperture within one of the first and second portions for receiving an implantable component of the medical device.

In certain aspects, the aperture may enable electrical contact between the implantable component and another component of the medical device.

In certain embodiments of the present disclosure, a medical device assembly configured for temporary positioning on the body of a host may comprise a medical device having a housing, and a mounting unit adapted for mounting on the skin of a host and for releasably retaining the housing of the medical device in a low-profile position on the host, wherein the mounting unit comprises a displaceable portion and wherein displacement of the displaceable portion at least partially releases the medical device housing from the mounting unit.

In certain aspects, the displacement provided by the displaceable portion may comprise one or more of linear, axial and angular movement.

In certain aspects, the displaceable portion may be configured to be displaced by low-force pressure against the displaceable portion in a direction away from the medical device.

In certain aspects, the medical device may include a feature for releasably coupling with a corresponding feature of the mounting unit.

In certain aspects, displacement of the displaceable portion of the mounting unit may decouple the corresponding features of the mounting unit and the medical device.

In certain aspects, the medical device may comprise a second feature for releasably coupling with a corresponding second feature of the mounting unit, wherein displacement of the displaceable portion of the mounting unit does not decouple the second corresponding features of the mounting unit and the medical device.

In certain aspects, the mounting unit may have a top surface for retaining a medical device and a bottom surface for placement on a skin surface.

In certain aspects, the bottom surface of the mounting unit may comprise an adhesive material.

In certain aspects, the top surface of the mounting unit may comprise at least one feature for releasably coupling to a corresponding feature of the medical device.

In certain aspects, the at least one feature of the mounting unit may be at least one rail and the at least one feature of the medical device is at least one groove.

In certain aspects, the at least one feature of the mounting unit may be a receptacle and the at least one feature of the medical device is a tab.

In certain embodiments of the present disclosure, a method of using an on body medical device may comprise mounting a medical device on the body of a host by means of a mounting unit affixed to a skin surface of the host, operatively using the medical device for a predetermined period of time, and displacing a first portion of the mounting unit relative to a second portion of the mounting unit from a first position to a second position, wherein displaying the first portion relative to the second portion at least partially releases the medical device from the mounting unit.

Certain aspects may comprise replacing at least one component of the medical device, returning the displaced first portion of the mounting unit to the first position, and operatively reusing the medical device for the predetermined period of time.

Certain aspects may comprise removing the medical device from the mounting unit, replacing at least one component of the medical device, mounting the medical device on the body of the host by means of a second mounting unit affixed to a second location on the skin surface of the host, and operatively reusing the medical device for the predetermined period of time.

In certain aspects, the medical device may be an analyte monitoring device comprising an electronics unit having a low-profile housing, and a plurality of at least partially implantable analyte sensors, each sensor being usable for the predetermined time period, wherein the mounting unit enables electrical coupling between the electronics unit and one of the plurality of analyte sensors.

In certain aspects, replacing at least one component of the medical devices may comprise replacing a used sensor with an unused sensor.

In certain aspects, the predetermined time period may be from about 1 day to about 30 days.

In certain aspects, displacing the first portion of the mounting unit relative to the second portion may comprise one or more of linear, axial and angular movement.

In certain aspects, displacing the first portion of the mounting unit relative to the second portion may comprise applying a low-force pressure against the first portion in a direction away from the medical device.

In certain aspects, at least partially releasing the medical device from the mounting unit may comprise decoupling a mating feature of the mounting unit from a corresponding mating feature of the medical device.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A holder apparatus for holding an on-body medical device, the on-body medical device having an enclosure housing one or more electronic components, the holder apparatus comprising:
a support body having a bottom portion configured to contact the skin of the user of the medical device, and a top portion to operably mount the enclosure of the medical device, wherein the support body comprises:
a first portion; and
a second portion moveable relative to the first portion; wherein the first and second portion of the support body interpose the enclosure of the medical device and the skin of the user, wherein at least the first portion is attachable to the skin of the user, and wherein the top portion of at least the first portion being configured to engage the enclosure of the medical device to hold the medical device in place on the support body, wherein the first and second portions having a medical device holding state in which the first and second portions are linearly aligned with respect to each other along the skin of the user of the medical device while at least the first portion is engaged with the enclosure of the medical device to hold the medical device in place on the support body, wherein movement of the second portion of the support body relative to the first portion of the support body and the enclosure of the medical device when the first portion is attached to the skin of the user and engaged with the enclosure of the medical device causes the first and second portions of the support body to transition to a medical device release state in which the first and second portions of the support body are linearly misaligned or offset with respect to each other and at least a portion of the enclosure of the medical device is released from the second portion of the support body while the enclosure of the medical device remains engaged with the first portion and operatively mounted on the support body.

2. The apparatus of claim 1, further comprising a third portion extending between the first and second portions, wherein the third portion is configured to be alterable from a first state to a second state to provide the movement of the second portion relative to the first portion.

3. The apparatus of claim 2, wherein the third portion is one of breakable, bendable, frangible or one or more combinations thereof.

4. The apparatus of claim 2, wherein the third portion comprises one or more of a reduced mass, a reduced thickness, a weakened area, a detent, a hinge, a fracture point or scoring.

5. The apparatus of claim 2, wherein the third portion is returnable to the first state upon being altered to the second state.

6. The apparatus of claim 2, wherein the third portion is not returnable to the first state upon being altered to the second state.

7. The apparatus of claim 1, wherein the relative movement comprises one or more of linear, axial and angular displacement.

8. The apparatus of claim 1, further comprising at least one feature for releasably coupling with a corresponding at least one feature of the medical device.

9. The apparatus of claim 1, wherein the first and second portions including a first surface configured to operably mount a bottom surface of the medical device.

10. The apparatus of claim 9, wherein the first and second portions including a second surface for placement on a skin surface, wherein the first and second surfaces are on opposing sides of the first and second portions.

11. The apparatus of claim 10, wherein the second surface comprises an adhesive.

12. The apparatus of claim 1, wherein the first portion comprises an abutment for retaining the medical device.

13. The apparatus of claim 1, further comprising an aperture within one of the first and second portions for receiving an implantable component of the medical device.

14. The apparatus of claim 13, wherein the aperture enables electrical contact between the implantable component and another component of the medical device.

15. The apparatus of claim 1, wherein movement of the second portion relative to the first portion further causes at least initiating movement of the medical device in a release direction from the first portion.

16. An on-body medical device assembly comprising:
a medical device having a housing and one or more electronic components positioned within the housing; and
a mounting unit adapted for mounting on a skin surface of a user of the medical device and for releasably retaining the housing of the medical device on the mounting unit,
wherein the mounting unit comprises a support body having a bottom portion configured to contact the skin of the user of the medical device, and a top portion to operably mount the housing of the medical device, the support body comprising a main portion and a displaceable portion, wherein each of the main and displaceable portions interposes the housing of the medical device and the skin of the user, wherein at least the main portion is attachable to the skin surface, and wherein the top portion of at least the main portion is configured to engage the medical device housing to hold the medical device in place on the support body,
wherein the main and displaceable portions having a first state in which the main and displaceable portions are linearly aligned with respect to each other along the skin of the user of the medical device while at least the first portion is engaged with the medical device housing to hold the medical device housing in place on the support body, and
wherein displacement of the displaceable portion of the support body relative to the main portion of the support body and the medical device housing of the medical device when the main portion is attached to the skin surface of the user and engaged with the medical device housing causes the main and displaceable portions of the support body to transition to a second state in which the main and displaceable portions of the support body are linearly misaligned or offset with respect to each other and at least a portion of the medical device housing is released from the displaceable portion of the support body of the mounting unit while the medical device housing remains engaged with the main portion and operatively mounted on the support body.

17. The assembly of claim 16, wherein the displacement provided by the displaceable portion comprises one or more of linear, axial and angular movement.

18. The assembly of claim 17, wherein the displaceable portion is configured to be displaced by a low-force pressure against the displaceable portion in a direction away from the medical device.

19. The assembly of claim 16, wherein the medical device includes a feature for releasably coupling with a corresponding feature of the mounting unit.

20. The assembly of claim 19, wherein the displacement of the displaceable portion of the mounting unit decouples the corresponding feature of the mounting unit and the medical device.

21. The assembly of claim 20, wherein the medical device comprises a second feature for releasably coupling with a corresponding second feature of the mounting unit, wherein the displacement of the displaceable portion of the mounting unit does not decouple the second corresponding feature of the mounting unit and the medical device.

22. The assembly of claim 16, wherein the main and displaceable portions of the mounting unit have a top surface to operably mount a bottom surface of the medical device housing and a bottom surface for placement on the skin surface.

23. The assembly of claim 22, wherein the bottom surface of the mounting unit comprises an adhesive material.

24. The assembly of claim 22, wherein the top surface of the mounting unit comprises at least one feature for releasably coupling to a corresponding feature of the medical device.

25. The assembly of claim 24, wherein the at least one feature of the mounting unit is at least one rail and the at least one feature of the medical device is at least one groove.

26. The assembly of claim 24, wherein the at least one feature of the mounting unit is a receptacle and the at least one feature of the medical device is a tab.

27. The assembly of claim 16, wherein displacement of the displaceable portion further causes at least initiating movement of the medical device in a release direction from the main portion.

28. A method of using an on body medical device, the method comprising:
mounting a medical device on a skin surface of a user with a mounting unit, the medical device having a housing and one or more electronic components positioned within the housing, the mounting unit comprising a support body having a bottom portion configured to contact the skin of the user of the medical device, and a top portion to operably mount the housing of the medical device, the support body including first and second portions, wherein each of the first and second portions of the support body interposes the housing of the medical device and the skin of the user, wherein at least the first portion is attachable to the skin surface, and wherein the top portion of at least the first portion is configured to engage the housing of the medical device to hold the medical device in place on the support body;
operatively using the medical device for a predetermined period of time; and
displacing the second portion of the mounting unit relative to the housing of the medical device and the first portion of the mounting unit when the first portion is attached to the skin of the user and engaged with the housing of the medical device transitioning the first and second portions from a first position in which the first and second portions are linearly aligned with respect to each other along the skin of the user of the medical device while at least the first portion is engaged with the housing of the medical device to hold the medical device in place on the support body, to a second position in which the first and second portions of the support body are linearly misaligned or offset with respect to each other, wherein displacing the second portion of the support body relative to the first portion of the support body and the housing of the medical device when the first portion is attached to the skin and engaged with the housing of the medical device releases at least a portion of the housing of the medical device from the second portion of the support body of the mounting unit while the housing of the medical device remains engaged with the first portion and operatively mounted on the support body.

29. The method of claim 28, further comprising:
replacing at least one component of the medical device;
returning the displaced second portion of the mounting unit to the first position; and
operatively reusing the medical device for the predetermined period of time.

30. The method of claim 29, wherein the medical device is an analyte monitoring device comprising an electronics unit having a low-profile housing, and a plurality of at least partially implantable analyte sensors, each sensor being usable for the predetermined period of time, wherein the mounting unit enables electrical coupling between the electronics unit and one of the plurality of analyte sensors.

31. The method of claim 28, further comprising:
removing the medical device from the mounting unit;
replacing at least one component of the medical device;
mounting the medical device on the skin surface with a second mounting unit affixed to a second location on the skin surface; and
operatively reusing the medical device for the predetermined period of time.

32. The method of claim 31, wherein the medical device is an analyte monitoring device comprising an electronics unit having a low-profile housing, and a plurality of at least partially implantable analyte sensors, each sensor being usable for the predetermined period of time, wherein the mounting unit enables electrical coupling between the electronics unit and one of the plurality of analyte sensors.

33. The method of claim 28, wherein displacing the first portion of the mounting unit relative to the second portion comprises one or more of linear, axial and angular movement.

34. The method of claim 28, wherein displacing the second portion of the mounting unit relative to the second portion and the medical device comprises applying a low force pressure against the second portion in a direction away from the medical device.

35. The method of claim 28, wherein releasing at least a portion of the medical device from the second portion of the mounting unit comprises decoupling a mating feature of the mounting unit from a corresponding mating feature of the medical device.

36. The assembly of claim 16, further including an analyte sensor coupled to the medical device housing, the analyte sensor including a plurality of electrodes, wherein the plurality of electrodes include a working electrode comprising an analyte-responsive enzyme and a mediator, wherein at least one of the analyte responsive enzyme and the mediator is chemically bonded to a polymer disposed on the working electrode, and wherein the at least one of the analyte-responsive enzyme and the mediator is crosslinked with the polymer.

37. The method of claim 28, wherein the analyte sensor includes a plurality of electrodes, wherein the plurality of electrodes include a working electrode comprising an analyte-responsive enzyme and a mediator, wherein at least one of the analyte-responsive enzyme and the mediator is chemically bonded to a polymer disposed on the working electrode, and wherein the at least one of the analyte responsive enzyme and the mediator is crosslinked with the polymer.

38. The method of claim 28, wherein displacing the second portion of the mounting unit relative to the first portion of the mounting unit from the first position to the second position further comprising at least initiating movement of the medical device in a release direction from the first portion.

* * * * *